United States Patent [19]

Thomas et al.

[11] 4,215,478
[45] Aug. 5, 1980

[54] DENTAL HYGIENE FLOSSING SYSTEM

[76] Inventors: Louis O. Thomas, 4745 Convention St., Baton Rouge, La. 70806; Raymond E. Boudreaux, 4155 Essen La., Apt. 81, Baton Rouge, La. 70809

[21] Appl. No.: 883,831

[22] Filed: Mar. 6, 1978

[51] Int. Cl.² ........................ A61C 3/00; A61C 15/00
[52] U.S. Cl. .................................... 433/25; 132/89; 132/93; 433/216
[58] Field of Search .................. 32/40 R; 132/89, 93, 132/91, 29; 427/2; 206/368, 369; 223/99; 15/104.5, 104.51, 104.8

[56] References Cited

U.S. PATENT DOCUMENTS

| | | | |
|---|---|---|---|
| 2,612,177 | 9/1952 | Footer | 132/93 |
| 3,775,848 | 12/1973 | Barnett | 32/40 |
| 3,896,824 | 7/1975 | Thornton | 132/89 |
| 3,930,059 | 12/1975 | Wells | 427/2 |
| 3,942,539 | 3/1976 | Corliss et al. | 132/91 |
| 3,943,949 | 3/1976 | Ashton et al. | 132/89 |
| 4,008,727 | 2/1977 | Thornton | 132/89 |
| 4,011,658 | 3/1977 | Tarrson et al. | 32/40 R |

*Primary Examiner*—Louis G. Mancene
*Assistant Examiner*—Michael J. Foycik, Jr.
*Attorney, Agent, or Firm*—Thomas S. Keaty; Charles C. Garvey, Jr.

[57] ABSTRACT

An article of manufacture for use in dental hygiene is disclosed. The device provides a leader, to which there is attached a thicker "mop" which can be comprised of a plurality of individual string members. The string members can be abrasive to enhance cleaning action. The several string members which form the "mop" would preferably have some absorbent quality in order to retain a desired therapeutic aid such as fluoride or the like. The strings could be alternatively fluoride impregnated. In use, the leader is first passed between gaps in the teeth until the "mop" portion contacts the gap. Sliding action of the abrasive mop between the teeth removes undesirable plaque and massages the gums. In the method of the present invention, individual thread members are added to the leader so that as many strings are placed between the teeth as possible without causing discomfort and the space between the teeth can be filled.

5 Claims, 8 Drawing Figures

DENTAL HYGIENE FLOSSING SYSTEM

BACKGROUND OF THE INVENTION

1. Field of the Invention

The present invention relates to articles for use in dental hygiene and techniques of dental hygiene and more particularly the present invention relates to a dental hygiene method and apparatus which cleans the spaces between the teeth of food particles, plaque and related undesirable deposits and growths.

2. General Background and Prior Art

Peridontal Disease (pyorrhea)

Gum disease is common to everyone. It actually begins when teeth first erupt and is present through life. Even though gum disease is present with the baby teeth, the teeth are not in the mouth long enough to be lost as a result. When the permanent teeth arrive, gum disease also begins and after a period of ten to twenty years, damage to the gum usually occurs. Ninety-five percent or more of all gum disease occurs between the teeth primarily because no one effectively cleans these areas. Even though you may use conventional dental floss, it is probable that you are not removing the poisonous bacterial film that is growing on the tooth. If you are not, gum disease (pyorrhea) will surely exist.

Gum disease is actually a slight inflammation of the gums which usually goes unnoticed. This slight inflammation in the gum tissue will cause pyorrhea pockets over a long period of time, usually between the teeth. These pockets that form between the gum and the tooth are called gum pockets, pyorrhea pockets, or periodontal pockets. As pockets deepen they become more and more infected causing loss of supporting bone until eventually the tooth is lost through abscess or looseness.

Presently the most commonly used item for cleaning the space between the teeth is conventional dental floss. Such dental floss comes in a variety of sizes, but is generally a single piece of string or cord which can be provided with a waxed outer surface. The conventional floss is of some utility, however it requires that the user move it in an up and down motion which is an awkward movement for the average user. Additionally, because of the reduced diameter of the floss, it does not do a complete job of cleaning between the teeth where there may be an exceptionally large space.

Several devices have been patented which have attempted to solve the problem of peridontal disease and like afflictions of the gums and teeth. The following table provides 20 listing of some prior art dental implements and like devices which are known to the applicant.

| PRIOR ART PATENTS | | |
|---|---|---|
| PATENT NO. | INVENTOR | ISSUE DATE |
| 1,069,874 | F. Z. Hanscom | Aug. 12, 1913 |
| 1,149,376 | W. A. Leonard & S. W. Boynton | Aug. 10, 1915 |
| 1,285,988 | G. H. & E. D. Gudebrod | Nov. 26, 1918 |
| 1,637,153 | J. A. Lawton | Oct. 23, 1926 |
| 2,522,794 | B. M. Medof | Feb. 8, 1950 |
| 2,612,177 | J. Footer | Sept. 30, 1952 |
| 3,930,059 | R. L. Wells | Dec. 30, 1975 |
| 694,557 | | |
| 982,510 | | |

General Discussion of the Present Invention

The present invention provides an oral hygiene method and apparatus which comprises a semi-rigid leader to which is attached a "mop", the "mop" providing an absorbent plurality of individual string members which have a larger diameter than the leader itself.

A connection holds the plurality of string members which form the "mop" to the leader string. Each string member can be comprised of a plurality of smaller threads which are stranded together in a spiral construction for example.

The object of the method of the present invention is to place as many threads between the teeth as possible without causing discomfort so that the space between the teeth will be filled. This will greatly improve cleaning efficiency.

With the method of the present invention, a preformed leader member with a loop is used, or one string is taken and looped together with about a length of the leader. This is done by laying the string down flat and crossing the length of leader over [+]. Picking up the two ends of the string simultaneously will cause the leader to loop over it. A knot can be tied in the loose ends of the leader to keep it from slipping.

The leader is placed between two lower bicuspid teeth for example, then cotton string pulled into position. "Shoe-shine" motion is then applied on each surface of each tooth and then the string pulled through. If the string slips through without resistance, another string should be added and the area rechecked. Repeat this until the number of strings most suitable is found. Most mouths will require varying amounts of string in different areas. The largest spaces are cleaned first, a string removed and the next smallest spaces cleaned and so on down to the smallest space. There will be some areas, especially in the front of the mouth, where a single string will not pass through. In these spaces, the string is split to the smaller threads to get the appropriate size that is needed.

BRIEF DESCRIPTION OF THE DRAWINGS

For a further understanding of the nature and objects of the present invention, reference should be had to the following detailed description, taken in conjunction with the accompanying drawings, in which like parts are given like reference numerals and wherein.

DETAILED DESCRIPTION OF THE PREFERRED EMBODIMENT

Figure 1:
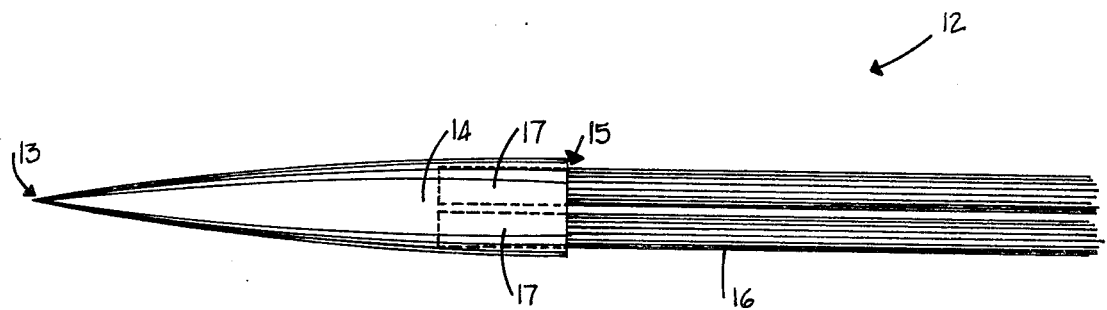
FIG. 1 is an enlarged, partial front view of the preferred embodiment of the dental hygiene device of the present invention illustrating the leader tip and its connection to the waxed leader line.
Figure 2:
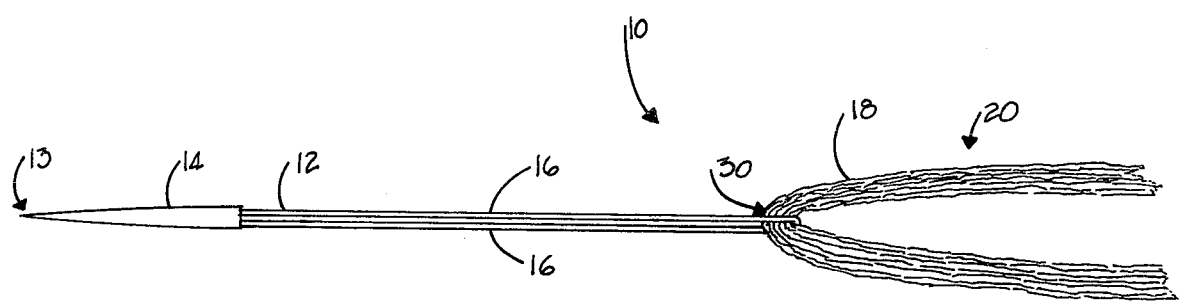
FIG. 2 is a front view of the preferred embodiment of the article shown in FIG. 1.

As can best be seen in FIGS. 1 and 2, the preferred embodiment of the dental hygiene device of the present invention designated generally by the numeral 10 is comprised of a leader assembly 12 and a "mop" member 20.

Leader assembly 12 is comprised of a tip 14 and a flexible leader line 16 forming a loop as can be seen in FIG. 2. As can best be seen in FIG. 1, leader line 16 can be attached to tip 14 by anchoring the tip portions 17 of leader line 16 within the opening 15 provided at the enlarged end portion of tip 14. A suitable connection could be made by means of glue or the like, or the tip portions 17 of lead line 16 could be integrally molded and manufactured with tip 14.

Leader line 16 may be waxed or unwaxed small diameter nylon thread such as existing unwaxed nylon floss. Tip 14 may be tapered as described above and as shown in FIGS. 1 and 2, or it may alternatively be of the same diameter throughout. Tip 14 in operation may be inserted between teeth splinted or not splinted and under bridges in order to place the "mop" 20 material in its cleaning position. Leader 16 may be inserted between teeth, thus enabling the user to pull the "mop" 20 between the teeth so that effective cleaning can take place. Cleaning would be effected by the user by sliding the "mop" structure 20 in a shoeshine fashion. Tip 14 could be square, round, oval, or flat. It could be tapered at either end with the larger diameter in the middle, or it may be of the same size throughout. The leader 16 could be bonded to the tip 14 or may be of the same plastic material, thereby providing a leader 16 of integral construction.

It should be understood thus that the prime purpose of leader 16 is for the purpose of positioning the "mop" structure 20 either between the teeth or under bridges so that cleaning can then subsequently take place.

In FIG. 2, there can be seen leader assembly 12, in which leader line 16 is "doubled" to form a loop and "mop" assembly 20 comprising a plurality of strings 18 is caught and held within the doubled lead line 16 at connection 30.

A plurality of string members 18 could be used to form "mop" 20. It should be understood, however, that it is desired to have "mop" 20 which is of an enlarged diameter and of an absorbent material. Thus, similar structures to the plurality of strings 18 shown in FIGS. 2 and 3 could be used to form a "mop" 20 within the spirit and teaching of the present invention. It is not necessary that each individual string 18 be absorbent but only that the entire "mop" assembly 20 have liquid retaining ability as is desirable. Alternatively, the individual string members could be impregnated with a desirable therapeutic agent such as fluoride or the like.

Figure 3:
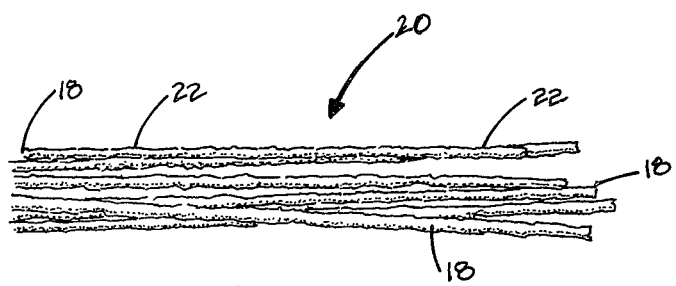
FIG. 3 is a partial view of the "mop" portion of the article shown in FIG. 2, illustrating the coarse texture of the plurality of the multiple thread members.

As can best be seen in FIG. 3, "mop" 20 is comprised of a plurality of individual strings 18. In the preferred embodiment, these strings 18 are provided with smaller projections 22 on their surface so as to give a roughened or abrasive effect. String 18 could be manufactured of any abrasive, unwaxed material such as cotton thread, for example. The cotton thread could be impregnated with fluoride to help sensitive teeth and aid in decay protection.

Tip 14 could be manufactured of any hard, yet semi-flexible material such as plastic. It would be desirable that tip 14 and leader 15 not be of a material which would cause permanent injury to the teeth and gums, but only remove the undesirable plaque. Leader line 16 could be of a plastic material or a waxed or unwaxed nylon or similar material.

In contrast to leader 16, "mop" 20 could be provided as an absorbent structure into which fluoride containing or like therapeutic fluids could be held and transferred to the desired area between the teeth during use of the device. Alternatively, the "mop" could be impregnated with desired therapeutic agents. An inspection of FIG. 2 shows that the device is inserted with the point 13 portion of tip 14 first to the area between the teeth. Thus, a very small, if not negligible, diameter which is capable of fitting into virtually any space between the teeth is provided. Leader 16 and tip 14 could have diameters for example of approximately one millimeter. However, various diameters could be provided to fit the needs of different age and size users. It can be seen that the diameter enlarges as tip 14 is passed between two teeth by the user until the enlarged end portion of tip 14 is reached. At this point, a maximum diameter is reached on tip 14. Tip 14 thus provides a means for preliminarily enlarging the space between the teeth and making ready at least some opening through which the enlarged "mop" 20 can then pass. The tip 14 may also be the same diameter throughout as well as tapered as described in FIG. 1. Since the tip 14 will be relatively hard, having some shape retaining characteristic (as is the case with injunction molded plastic, for example), it would be able to overcome any resistance of the gums and enlarge an opening sufficient for "mop" 20 to pass therethrough. The "mop" structure 20 could have an effective diameter substantially the same as, or larger than, the diameter of tip 14 at its greatest diameter. Thus, all of the area about the opening between the teeth would be cleaned and scraped as "mop" 20 passed therethrough (Note FIG. 5).

When the "mop" 20 portion of the device comes into the space existing between the teeth, the operator can use the leader 12 to pull on the multiple string members 18 which comprise the "mop" 20 in a "shoe-shine" motion. Such a side-to-side motion would be much easier and more effective than the up-and-down motion (See FIG. 6) generally required in the use of conventional dental floss. This feature would make the device of the present invention much more effective than conventional dental floss in the hands of the average person. The multiple strings 20 would provide preferably a more abrasive surface than any other nylon or like interdental product presently in use and therefore a greater quantity of dental plaque and like undesirable deposits would be removed during its use. It is the dental plaque which is the principal cause of dental cavities and peridontal disease. Likewise, the gums would be massaged as is desirable.

The plastic or like semi-hard tip 14 allows the device to be threaded through the smallest openings underneath bridges, and other obstructions in the mouth. The mop provides an enlarged diameter cleaning surface which can change shape and conform to virtually the shape of any openings, the plurality of threads 18 merely shifting position to effect the necessary cross-sectional change of shape.

The device could be impregnated with any desired therapeutic aid as well as an agent which would make its use more palatable, such as a flavoring for example. The basic device could be altered by adding or substracting greater or lesser amounts of thread members 20 into the leader 12. Unlike conventional dental floss, the "mop" 22 would place medication or like therapeutic aids directly against the inter-dental spaces, i.e., those portions of the mouth most susceptible to dental cavities and peridontal disease.

Figure 4:
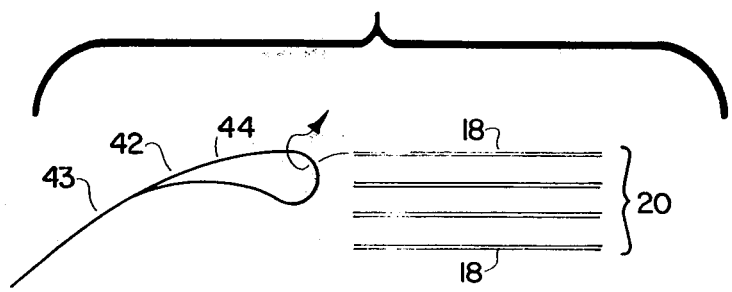
FIG. 4 is a perspective view of a first alternative embodiment of the apparatus of the present invention.

FIG. 4 illustrates a second alternative embodiment of the apparatus of the present invention designated generally by the numeral 40. In FIG. 4 there can be seen an integrally formed leader member 42 which is comprised of a leader tip 43 and a loop 44. The leader member 42 can be formed integrally of plastic or like construction. The integrally formed leader 42 provides a loop 44 through which individual thread members 46 can be passed. Note the curved arrow 47 in FIG. 4 illustrating the method of attaching the individual string members 46 to the loop structure 44 of leader 42. Such an integrally formed leader member would be formed of a minimal diameter such as for example, one millimeter so that it can easily fit between spaces in the teeth, under bridges, and the like.

Figure 7:
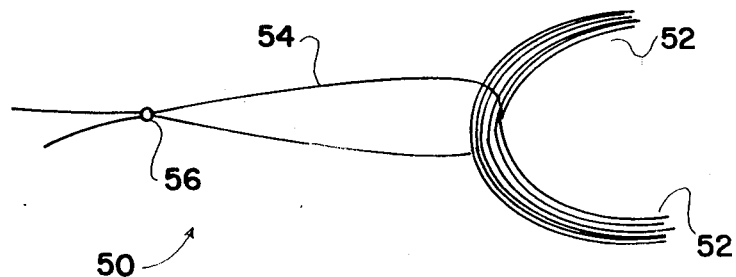
FIG. 7 is a perspective view of a second alternative embodiment of the apparatus of the present invention.

FIG. 7 illustrates a second alternative embodiment of the apparatus of the present invention designated generally by the numeral 50. In FIG. 7 there can be seen a plurality of string members 52 which are attached to a leader structure 54. The leader 54 is formed by tying a single piece of floss material for example, in a knot 56. The knot 56 forms a loop 54 through which a plurality of string members 52 can be threadably attached. The floss loop leader 54 can then be forced in between the teeth and pulled by the hand. The pulling action will bring the string members 52 into contact with the inter-dental space as is desirable (Note FIG. 5).

METHOD OF USE

Figure 4A:
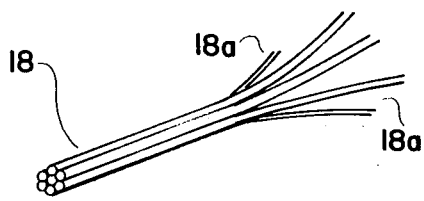

To use the apparatus 10 of the present invention, there is needed a leader structure such as is provided in FIGS. 1, 2, 4 and 7. The leader structure is provided with the desired number of individual string members 18. The desired number of strings 18 is looped over the leader 16 as is illustrated in FIGS. 2, 4 and 7. Most mouths will require varying amounts of string 18 in different areas. In the method of the present invention, the largest spaces are first cleaned. Thus, an individual after a certain amount of use and practice will determine which spaces between his teeth are largest and will clean these first. As the user progressively cleans the spaces between all of the teeth, he will gradually move toward the next smallest spaces between the teeth until he finishes cleaning his teeth by cleaning the smallest space between teeth in his mouth. When the user comes to an area where a plurality of strings will not pass between the space of two teeth, a string member 18 is removed from the leader and the reduced over-all space provided in cross-section to "mop" 20 is reduced. It will be understood that following this method each space from the largest inter-dental space to the smallest in the user's mouth will be able to be cleaned. There may be some areas, especially in the front of the mouth, where a single string structure may not pass through. In such spaces, an individual string 18 can be split since a multiple strand structure is provided for each string 18. Note in FIG. 4a, where a plurality of threads 18a are used to form a single string 18. Thus, individual string members can be broken up into smaller units so that the appropriate size can be found for each inter-dental space.

Figure 5:
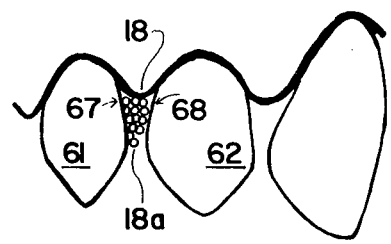
FIG. 5 is a front schematic view of a pair of teeth showing the thread members of the apparatus of the present invention filling the space therebetween.

The apparatus 10 is made by looping as many multiple "mop" strings as needed through the leader material 16 of apparatus 12. The "mop" may be placed in its cleaning position by inserting tip 14 between the teeth or under bridges and by pulling apparatus 12 through the teeth until the "mop" 20 is between the teeth. (See FIG. 5). Also, the "mop" may be placed in its cleaning position by inserting leader 16 of apparatus 12 between the teeth, as one would use conventional dental floss, again pulling apparatus 12 through the teeth until the "mop" 20 is positioned between the teeth as illustrated in FIG. 5. Once the "mop" is placed in this cleaning position between the teeth, it can be "shoe-shined" on each interdental surface or under the pontics of bridges until all the dental plaque is removed, after which time the "mop" 20 can be completely pulled through the gap, space, or the like.

The apparatus 40 shown in FIG. 4 can be used to clean primarily under bridges and between splinted teeth. Again, the user will begin with a maximum number of strings 18 that will comfortably go between the teeth and the plastic leader 42 will be used as the leader. Once the "mop" 20 is in place, a "shoe-shine" motion is used under the bridge, false tooth, or the like until the area is clean.

Figure 6:
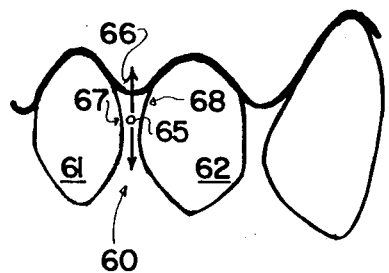
FIG. 6 is a front schematic view of a pair of teeth showing a prior art dental floss member and its method of cleaning the space between the teeth.

FIGS. 5 and 6 are illustrative of the space 60 which is seen between teeth 61, 62. Note in FIG. 6 that a conventional dental floss strand 65 is shown occupying the inter-dental space 60. Arrow 66 shows the upward and downward movement which is required in order to scour the inner edges 67, 68 of teeth 61, 62, respectively. Note however in FIG. 5 that the apparatus of the present invention provides a plurality of string members 18 which are comprised of individual thread members 18a. It can be seen by the schematic illustration of FIG. 5 that the inter-dental space 60 is substantially filled by the plurality of individual thread members 18a provided with the present invention. The plurality of threads 18a fill up and exactly conform to the inter-dental space 60. Note that the inner edge 67, 68 of teeth 61, 62 are in contact with and cleaned and scraped by the individual thread members 18a. This is most desirable and provides an especially effective method for cleaning the food particles, plaque, and like undesirable bacterial film and deposits from the inter-dental spaces.

Because many varying and different embodiments may be made within the scope of the inventive concept herein taught and because many modifications may be made in the embodiments herein detailed in accordance with the descriptive requirements of the law, it is to be understood that the details herein are to be interpreted as illustrative and not in a limiting sense.

What is claimed as invention is:

1. A dental hygiene device for cleaning interdental spaces comprising:
   a. a floss leader assembly adapted for hand placement and subsequent sliding movement between two adjacent teeth, said leader assembly comprising,
      (i) a tip member, said tip member being of a generally semi-flexible material; and
      (ii) a floss leader line attached to said tip member, said leader line being a string member having its end portions attached to said tip member, there being formed a loop by the attachment of said leader line to said tip member;
   b. an elongated "mop" connected to said leader assembly, said "mop" being comprised of a plurality of absorbant cotton threads arranged in a group, and doubled to temporarily attach said plurality of absorbant cotton threads to said floss leader assembly at said loop;

c. connection means for attaching said absorbant "mop" to said leader assembly, said connection means comprising said loop, each of said cotton threads being generally doubled and folded in half through said loop; and d. fluoride impregnation means for impregnating said plurality of absorbant cotton threads with a therapeutic fluoride agent.

2. The device of claim 1 wherein said group of absorbant cotton threads comprising said "mop" have a liquid retaining capability.

3. The device of claim 2, wherein said tip member is generally conically shaped, providing a minimal diameter pointed end portion and a larger diameter portion at the opposite end from said pointed end.

4. A method of dental cleaning of an interdental space between two adjacent teeth comprising the steps of:
a. providing a floss material leader line;
b. forming a loop with a portion of the leader line;
c. adding a plurality of absorbant cotton thread members to the loop by folding the cotton thread members in half across the loop;
d. impregnating the absorbant cotton thread members with a therapeutic fluoride agent;
e. placing the floss leader into the space between two adjacent teeth; and
f. pulling the floss leader and attached folded plurality of fluoride impregnated cotton thread members between the two adjacent teeth.

5. The method of claim 1 wherein there is provided the further step of sliding the "mop" structure back and forth in a "shoe-shine" fashion within the inter-dental space.

* * * * *